United States Patent [19]

Summers

[11] Patent Number: 4,994,067
[45] Date of Patent: Feb. 19, 1991

[54] DISTAL ATHERECTOMY CATHETER

[75] Inventor: David P. Summers, Montgomery, Tex.

[73] Assignee: American Biomed, Inc., The Woodlands, Tex.

[21] Appl. No.: 312,737

[22] Filed: Feb. 17, 1989

[51] Int. Cl.⁵ ........................ A61M 25/00; A61B 17/00
[52] U.S. Cl. ...................................... 606/159; 606/170; 604/22
[58] Field of Search ............... 606/106, 159, 170, 171; 604/27, 35, 49, 52, 53, 22

[56] References Cited

U.S. PATENT DOCUMENTS

| | | | |
|---|---|---|---|
| 3,448,741 | 6/1969 | Dennis et al. | 606/159 |
| 3,815,604 | 6/1974 | O'Malley et al. | 606/171 X |
| 3,844,272 | 10/1974 | Banko . | |
| 3,882,872 | 5/1975 | Douvas et al. . | |
| 3,884,238 | 5/1975 | O'Malley et al. . | |
| 3,937,222 | 2/1976 | Banko | 606/170 |
| 4,011,869 | 3/1977 | Seiler, Jr. . | |
| 4,111,207 | 9/1978 | Seiler, Jr. . | |
| 4,167,943 | 9/1979 | Banko . | |
| 4,167,944 | 9/1979 | Banko . | |
| 4,203,444 | 5/1980 | Bonnell et al. . | |
| 4,210,146 | 7/1980 | Banko . | |
| 4,323,071 | 4/1982 | Simpson et al. . | |
| 4,411,055 | 10/1983 | Simpson et al. . | |
| 4,513,745 | 4/1985 | Amoils . | |
| 4,577,629 | 3/1986 | Martinez . | |
| 4,589,412 | 5/1986 | Kensey . | |
| 4,589,414 | 5/1986 | Yoshida et al. . | |
| 4,598,710 | 7/1986 | Kleinberg et al. . | |
| 4,603,694 | 8/1986 | Wheeler . | |
| 4,616,648 | 10/1986 | Simpson et al. . | |
| 4,616,652 | 10/1986 | Simpson et al. . | |
| 4,631,052 | 12/1986 | Kensey . | |
| 4,651,753 | 3/1987 | Lifton . | |
| 4,661,094 | 4/1987 | Simpson et al. . | |
| 4,662,869 | 5/1987 | Wright . | |
| 4,669,469 | 6/1987 | Gifford, III et al. . | |
| 4,678,459 | 7/1987 | Onik . | |
| 4,681,106 | 7/1987 | Kensey et al. . | |
| 4,685,458 | 8/1987 | Leckrone . | |
| 4,696,667 | 9/1987 | Masch . | |
| 4,728,319 | 3/1988 | Masch . | |
| 4,729,763 | 3/1988 | Henrie . | |
| 4,747,406 | 5/1988 | Nash . | |
| 4,747,821 | 5/1988 | Kensey et al. . | |
| 4,749,376 | 6/1988 | Kensey et al. . | |
| 4,765,332 | 8/1988 | Fischell et al. . | |
| 4,771,774 | 9/1988 | Simpson et al. . | |
| 4,772,258 | 9/1988 | Marangoni et al. . | |
| 4,781,186 | 11/1988 | Simpson et al. . | |
| 4,784,636 | 11/1988 | Rydell | 606/159 X |
| 4,794,931 | 1/1989 | Yock . | |
| 4,819,635 | 4/1989 | Shapiro . | |
| 4,834,729 | 5/1989 | Sjostrom . | |
| 4,844,064 | 7/1989 | Thimsen et al. . | |
| 4,850,354 | 7/1989 | McGurk-Burleson et al. . | |

Primary Examiner—Robert A. Hafer
Assistant Examiner—Kerry Owens
Attorney, Agent, or Firm—Gunn, Lee & Miller

[57] ABSTRACT

A distal atherectomy catheter comprises a flexible outer catheter tube housing a reciprocal cutting element at its distal end. The cutting element is connected to an inner catheter tube concentrically located within the outer catheter tube. An annular passage defined between the inner and outer tubes provides a discharge passage communicating with an external vacuum mechanism for collection of excised material removed from the coronary vessel. A flexible drive shaft extending through the inner catheter tube terminates in a detachable cutting burr for boring through obstructions in the coronary vessel. The drive cable is connected to an external drive motor.

10 Claims, 2 Drawing Sheets

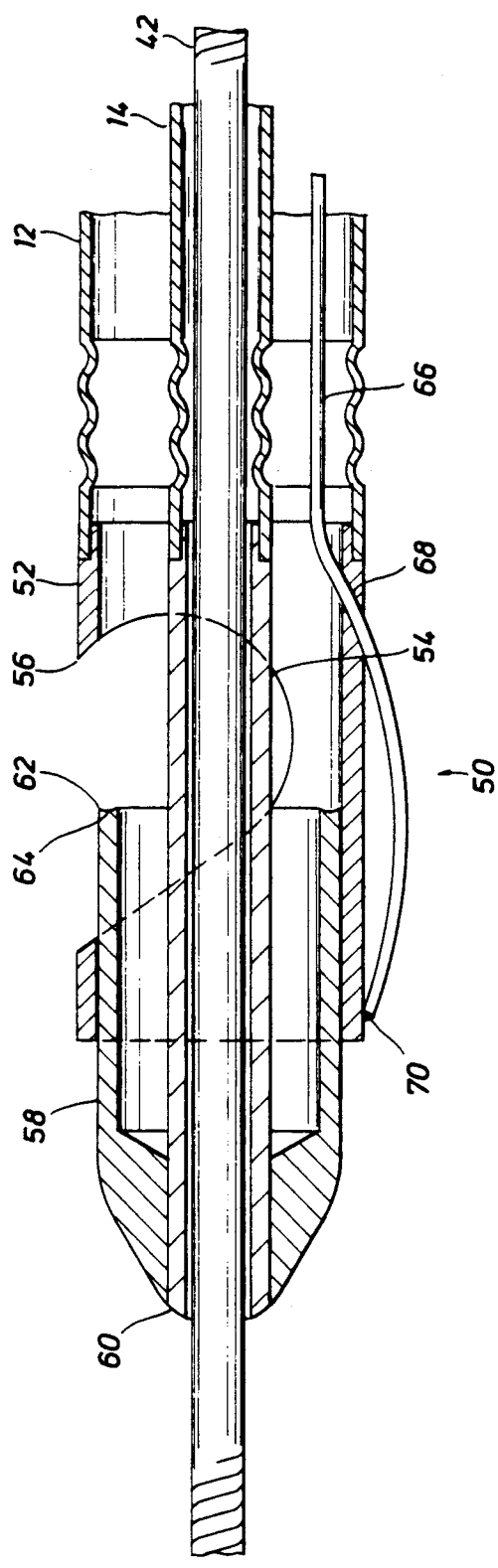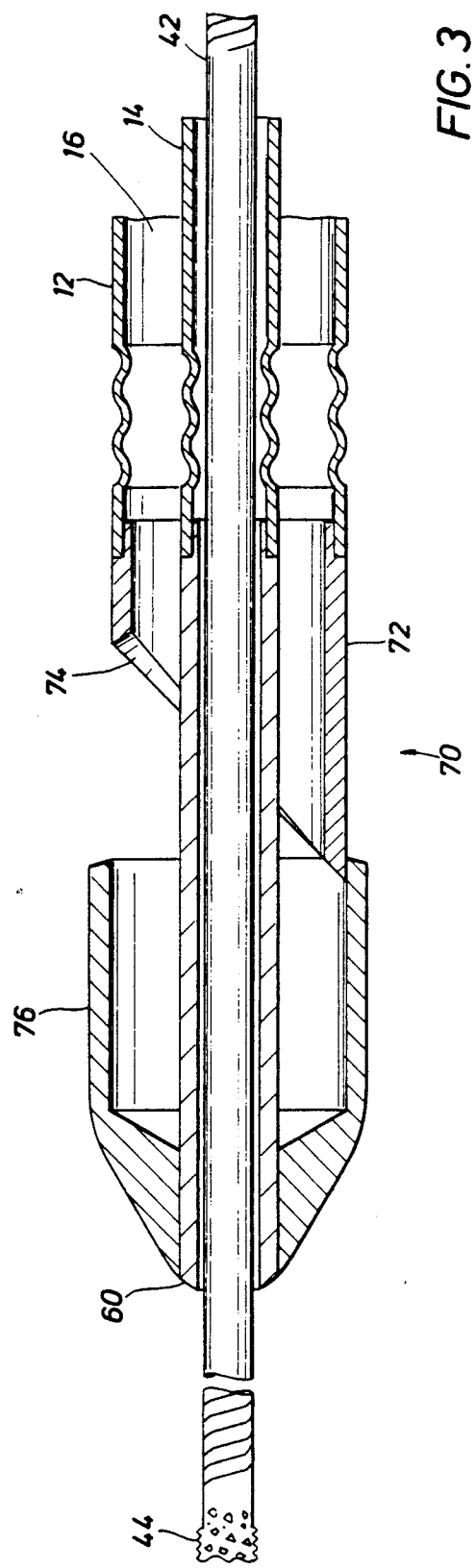

DISTAL ATHERECTOMY CATHETER

BACKGROUND OF THE DISCLOSURE

The present invention is directed to an atherectomy catheter, particularly, a distal atherectomy catheter for use in the distal and coronary arteries where small vessel size and tortuosity present numerous problems of access.

Many technological advancements have been made in recent years for treatment of coronary disease. Surgical bypass techniques such as cardiopulmonary bypass surgery is routinely performed and is highly successful. While the risks of bypass surgery have been minimized through technological advancements, opening of the chest cavity is required. This requires special surgical skills and equipment which are not readily available in many areas. In many patients, a bypass operation may not be indicated and therefore various surgical techniques have been devised to treat occlusive coronary artery disease of such patients. For example, various prior art devices have been developed for removing and/or compressing atherosclerotic plaque, thromboses, stenoses, occlusion, clots, embolic material, etc. from veins, arteries, and the like.

One such device is disclosed in U.S. Pat. No. 4,650,466 (Luther). Luther discloses an angioplasty device comprising a woven tube of metal or plastic fibers and a retraction stylet that are attached at one end of a catheter tube for insertion into a vein, artery and the like for the removal of plaque and similar material. One or more guide wires are attached to the woven tube for rotation and manipulation inside the artery. The woven tube is placed within the artery and expanded to contact the interior, plaque coated wall of the artery. Movement of the expanded woven tube abrades the plaque from the arterial wall to form particles which are trapped within the woven tubes. Removal of the angioplasty device from the artery removes the trapped plaque particles from the patient.

Other prior art devices include catheters fitted with an inflatable balloon for compressing occlusive materials such as plaque against the vessel wall. U.S. Pat. No. 4,273,128 (Lary) discloses a coronary cutting and dilating instrument for treatment of stenotic and occlusive coronary artery disease. The instrument disclosed therein includes a cutting and dilating instrument having one or more radially extending knife blades at a forward end thereof for making the coronary incision and an inflatable balloon for dilating the stenotic artery zone immediately after the incision.

Other angioplasty devices include a catheter having a motor driven cutting head mounted at its distal end. The cutting head is connected to the drive motor via a flexible drive shaft extending through the catheter. Extremely high rotational cutting head speeds have been achieved, in the range of two to three hundred thousand rpm, by these motor driven cutter heads. Various problems, however, have been associated with the use of balloon tipped catheters and high speed cutting heads. The balloon catheter is expanded by injection of pressurized fluid into the balloon to expand it against the wall of the artery. Some problems which have been reported include vessel dissection, perforation, rupture, conversion of a stenosis to an occlusion and embolization. Furthermore, angioplasty devices utilizing balloons do not remove the plaque from the arterial wall but simply compress the plaque against the wall of the vessel. Thus, the stenosis or occlusion frequently reoccur requiring further treatment.

Atherectomy devices utilizing motor driven high speed cutting head include a number of disadvantages. Heat dissipation and vibration is a problem. The path to the occlusion in an artery is often a tortuous path and therefore the flexible drive shaft connected to the cutter head must often traverse a number of bends or curves. Consequently, as the flexible drive shaft rotates, it contacts the inner wall of the catheter resulting in localized heating and vibrations due to the frictional contact. This, of course, is very uncomfortable for the patient and may result in weakening or perforation of the vessel.

It is therefore an object of the invention to provide an atherectomy catheter having a reciprocal cutter head at the distal end thereof.

It is another object of the invention to provide an atherectomy catheter for traversing the small and tortuous vasculature of the heart and having the ability to bore through a total obstruction and excise a hemispherical or circumferential section from the lumen of the vessel and entrap the excised section within a containment housing.

It is yet another object of the invention to provide an atherectomy catheter for progressively opening the lumen of a vessel, entrapping and discharging the excised specimen into a containment housing on the catheter until the entire obstruction has been removed leaving a smooth fissure and flap-free enlarged internal vessel diameter.

SUMMARY OF THE INVENTION

A distal atherectomy catheter is disclosed for removing obstructions, plaque, stenosis, occlusions, or the like from an artery or coronary vessel. The catheter comprises a flexible hollow outer catheter tube housing a reciprocal cutting element at its distal end. The cutting element is connected to an inner catheter tube concentrically located within the outer tube. An annular return passage is defined between the inner and outer tubes providing a discharge passage communicating with an external vacuum means for collection of cuttings. A flexible drive cable extends through the inner catheter tube terminating in a detachable cutting diamond or carbide burr for boring through obstructions in the vessel. The drive cable is connected to an external drive motor.

DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 2 is an enlarged sectional view of the cutting head of the invention; and

FIG. 3 is a sectional view of an alternate embodiment of the cutting head of the invention.

DETAILED DESCRIPTION OF THE PREFERRED EMBODIMENT

Figure 1:
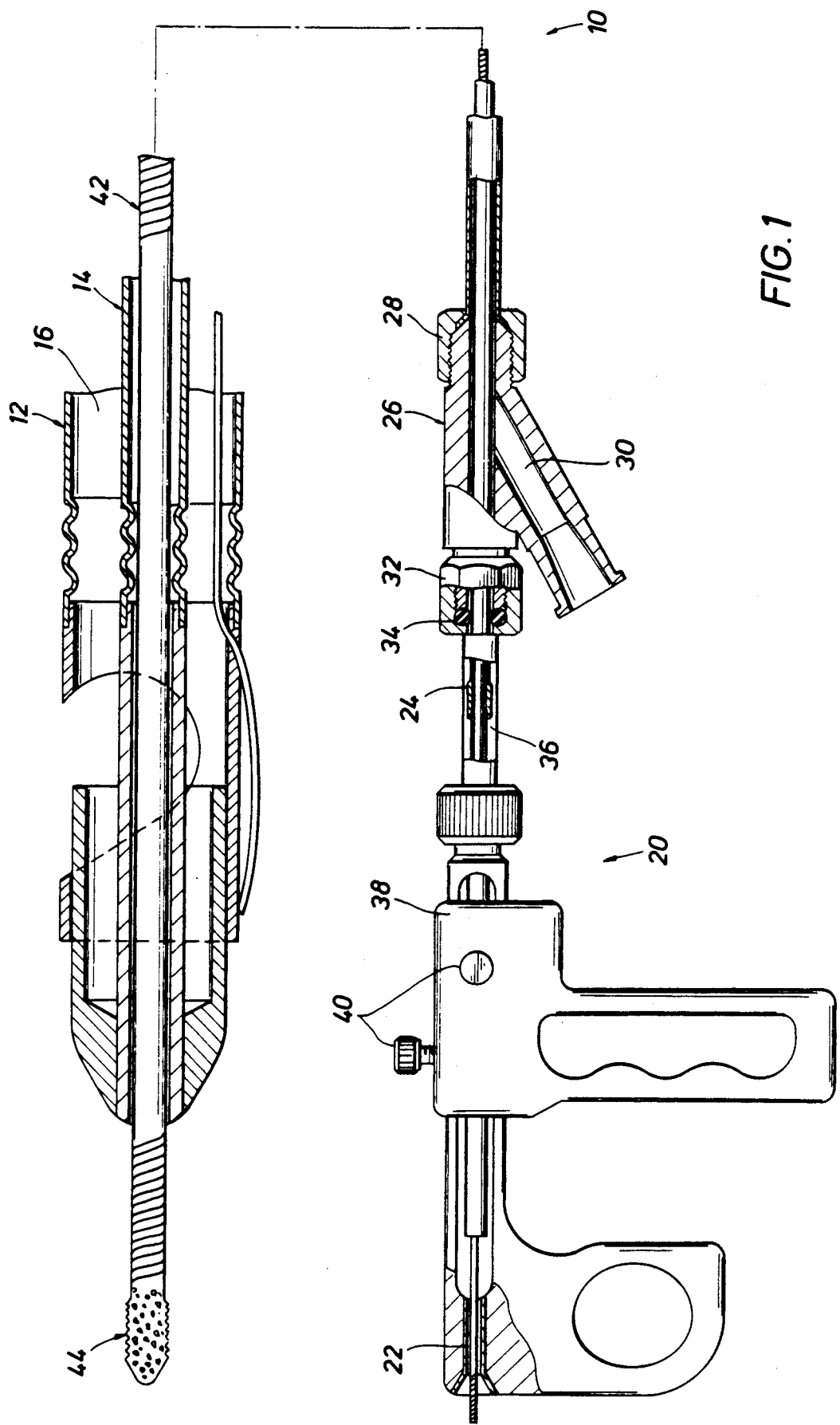
FIG. 1 is a partial sectional view of the apparatus of the invention.

Referring first to FIG. 1, the catheter of the invention is generally identified by the reference numeral 10. The catheter 10 of the invention comprises a flexible outer catheter tube 12 which may be several feet in length. Received within the outer catheter tube 12 is an inner catheter tube 14. The inner catheter tube 14 is concentrically located within the outer catheter tube 12 defining an annular passage 16 therebetween. The annular passage 16 provides a return passage for excised plaque or tissue removed from the arterior wall.

The proximal ends of the inner and outer catheter tubes 12 and 14 are connected to a hand-actuated manipulator assembly generally identified by the reference numeral 20. The manipulator assembly 20 comprises a handle 22 connected to a coupling 24 which is in turn connected to a "Y" fitting and pressure assembly 26. The pressure assembly 26 includes a flared tubing connector 28 which secures the end of the outer catheter tube 12 to the pressure assembly 26. The pressure assembly 26 branches to form a "Y" configuration. One branch of the pressure assembly 26 defines an outlet passage 30. The outlet passage 30 is connected to a vacuum source (not shown in the drawings) for removal of excised plaque or tissue to a collection vessel. A tubing connector 32 connects one end of the pressure vessel 26 to the coupling 24. An 0-ring 34 is compressed by the connector 32 about the inner catheter 14 thereby terminating the annular passage 16 so that excised plaque and tissue is directed through the outlet passage 30 to the collection vessel.

The inner catheter 14 extends through the pressure assembly 26 and is connected to an inner catheter manipulator 36 which extends into a longitudinal hollow and cut-out portion of the handle 22. A slide member 38 is securely fastened to the catheter manipulator 36 which connects to the inner catheter 14. The slide member 38 is spring biased for reciprocating the inner catheter 14 for excising plaque or tissue from the coronary vessel. Set screws 40 secure the slide member 38 to the catheter manipulator 36 and are adjustable to set the cutting length of the cutting head assembly.

The atherectomy catheter 10 of the invention as shown in FIG. 1 includes a flexible drive cable 42 which extends through the inner catheter 14 and terminates in a detachable cutting head or carbide burr 44. The drive cable 42 extends through the manipulator assembly 20 and is connected to an external drive source for rotating the drive cable 44 to bore through an obstruction in the coronary vessel. Boring may be accomplished at a relatively low RPM permitting the nose portion of the cutting head of the invention to be inserted into the bored lumen so that the obstruction may be excised.

Referring now to FIG. 2, the cutting head assembly 50 of the invention is shown in greater detail. The outer catheter tube 12 defines a sectioning blade 52. The blade 52 is formed by removing a section of the outer catheter tube 12 forming a port or slot permitting access to the interior of the outer catheter 12. The slot 54 defines a "duck bill" profile terminating at point 56. The duck bill profile aids in grabbing the tissue to be excised. As the tissue or obstruction material drops into the slot 54, it is pushed against the point 56 and speared and held stationary for removal by the slide cutter.

A slide cutter 58 is mounted to the distal end of the inner catheter tube 14. The slide cutter 58 defines a hollow substantially cylindrical body terminating in a nose portion 60 which is welded or bonded to the distal end of the inner catheter tube 14. The trailing or cutting end 62 of the sliding cutter 58 defines a circumferential cutting blade. The end 62 includes a groove 64 formed therein. The groove 64 has a sharp radius of curvature so that the external and internal edge of the end 62 define a circumferential, knife-like cutting surface.

In operation, the catheter 10 of the invention may be used to remove plaque or blockages from coronary arteries or vessels in the human body. For purposes of illustration, the following discussion will be directed to the use of the catheter 10 in removing an obstruction from a coronary artery. To this end, the catheter 10 is introduced into the body of the patient through a femoral artery or some other artery selected by the physician. The catheter 10 is pushed through the femoral artery to the site in the coronary artery requiring removal of an obstruction. Once the obstruction is reached, the drive cable 42 is rotated and advanced so that the burr 44 bores into the obstruction and the nose portion 60 is inserted in the bore formed by the burr 44 for dilating the vessel. As the catheter 10 advances through the vessel, the inner catheter 14 is retracted so that the slide cutter 58 reciprocates within the sectioning blade 52 of the outer catheter tube 12. This reciprocating motion excises a hemispherical or circumferential section of the obstruction and entraps the excised plaque or tissue within the annulus 16. Each excision progressively opens the vessel, excising and discharging sections of the obstruction into the annulus 16 until the entire obstruction has been removed. Upon removal of the obstruction, the coronary vessel has a smooth and flap free enlarged internal diameter.

The slot 54 is keyed to the manipulator assembly 20 so that its rotational position is known and the obstruction may be completely removed by rotating the atherectomy catheter of the invention 360° within the coronary vessel. To insure that substantially all of the obstruction is removed, a deflection wire 66 extends through the outer catheter tube 12 and exits the tube 12 at 68 and is welded to the forward end of the outer catheter tube 12 at 70. Manipulation of the deflection wire 66 permits the cutting head to be forced against the inner wall of the coronary vessel so that substantially all of the obstruction is removed and the internal diameter of the vessel is substantially free of any obstruction.

Insertion of the atherectomy catheter 10 through the femoral artery of the patient requires that it follow a tortuous path through bends and curves, in the coronary artery or vessel. To facilitate insertion of the catheter 10, sections of the inner and outer catheter tubing 12 and 14 include a bellowed portion, for example bellows 63 and 65 shown in FIG. 1-3. The bellows 63 and 65 entrance the flexibility of the catheter 10 so that it may more easily traverse the bends and curves encountered in the coronary artery or vessel.

Referring now to FIG. 3, an alternate embodiment of the cutting head assembly of the invention is disclosed. The cutting head assembly shown in FIG. 3 is substantially similar to the cutting head assembly of FIG. 1 and therefore like reference numerals are used to identify like elements. In the cutting head assembly 70 shown in FIG. 3, the outer catheter tube 12 includes a sectioning blade 72 mounted on the distal end thereof. The sectioning blade 72 is substantially cylindrical in shape and welded or otherwise bonded to the distal end of the outer catheter tube 12. The sectioning blade 72 includes an angled yet circumferential cutting surface 74 formed by cutting through the cylindrical body of the sectioning blade 72 at an angle of approximately 45°.

A slide cutter 76 is mounted to the distal end of the inner catheter tube 14. The slide cutter 76 defines a hollow substantially cylindrical body terminating in a nose portion 60 which is welded or bonded to the distal end of the inner catheter tube 14. The internal diameter of the slide cutter 58 is substantially equal to the external diameter of the sectioning blade 74 which is slidably received within the slide cutter 58 upon reciprocation. In operation, the cutting head assembly 50 operates in substantially the same manner as the cutting head assembly 50 shown in FIG. 2, however, the slide cutter 76 slides externally or about the sectioning blade 72 for excising the obstruction in the coronary vessel.

While the foregoing is directed to the preferred embodiments of the present invention, other and further embodiments of the invention may be devised without departing from the basic scope thereof, and the scope thereof is determined by the claims which follow.

What is claimed is:

1. An atherectomy catheter for removal of occlusive material in a coronary vessel, comprising:
   (a) an outer catheter tube;
   (b) an inner catheter tube concentrically received within said outer catheter tube and defining an annulus therebetween;
   (c) flexible drive shaft means extending through said inner catheter tube terminating in an abrasive burr for boring through an obstruction in the coronary vessel;
   (d) wherein said outer catheter tube and said inner catheter tube cooperate to form a cutting assembly for excising the occlusive material in the coronary vessel;
   (e) manipulator means connected to the proximal end of said outer catheter tube and said inner catheter tube for reciprocating said inner catheter tube relative to said outer catheter tube for excising the occlusive material in the coronary vessel; and
   (f) vacuum means connected to said manipulator means and said outer catheter for evacuating the excised occlusive material from the coronary vessel.

2. The apparatus of claim 1, wherein said outer catheter tube includes a sectioning blade formed on the distal end thereof for removing occlusive material from the coronary vessel.

3. The apparatus of claim 2, wherein said inner catheter tube includes a slide cutter mounted on the distal end thereof, said slide cutter being reciprocally received within said outer catheter tube and cooperating with said sectioning blade for excising occlusive materials from the coronary vessel.

4. The apparatus of claim 3, wherein said sectioning blade presents a duck bill profile for grabbing the occlusive material and holding it stationary for removal by said slide cutter.

5. The apparatus of claim 4, wherein said slide cutter includes a cutting end including a circumferential groove formed therein having a sharp radius of curvature defining external and internal edges forming a circumferential knife-like cutting surface.

6. The apparatus of claim 5, wherein said slide cutter includes a substantially hollow, cylindrical body terminating in a nose portion bonded about the distal end of said inner catheter tube.

7. The apparatus of claim 1, including deflection means having one end secured externally at the forward end of said outer catheter tube and extending interiorly of said outer catheter tube for deflecting said cutting assembly toward the interior wall of the coronary vessel.

8. The apparatus of claim 1, wherein said manipulator means comprises a handle and slide member connected thereto, said slide member being adjustably connected to the proximal end of said inner catheter tube and including spring bias means for reciprocating the inner catheter tube relative to said outer catheter tube.

9. The apparatus of claim 1, wherein said outer catheter tube and said inner catheter tube include flexure joint means permitting said cutting assembly to flex while traversing through the coronary vessel.

10. An apparatus for removing an obstruction in a vessel in the human body, comprising;
    (a) an outer catheter tube;
    (b) an inner catheter tube concentrically received within said outer catheter tube and forming an annulus therebetween;
    (c) flexible drive shaft means extending through said inner catheter tube terminating in an abrasive burr for boring through an obstruction blocking the vessel;
    (d) wherein said outer catheter tube and said inner catheter tube cooperate to form a cutting head assembly for excising the obstruction blocking the vessel;
    (e) manipulator means connected to the proximal end of said outer catheter tube and said inner catheter tube for reciprocating said inner catheter tube relative to said outer catheter tube;
    (f) vacuum means connected to said manipulator means and said outer catheter tube for evacuating the excised obstruction from the vessel via said annulus; and
    (g) deflection means having one end secured externally at the forward end of said outer catheter tube and extending interiorly of said outer catheter tube for deflecting said cutting head assembly toward the interior wall of the vessel.

* * * * *